United States Patent [19]
Abe et al.

[11] Patent Number: 5,476,883
[45] Date of Patent: Dec. 19, 1995

[54] PREPARATION PROCESS OF ACRYLAMIDE FROM PURIFIED ACRYLONITRILE

[75] Inventors: Takeya Abe; Yoshihiko Kambara, both of Takaishi, Japan

[73] Assignee: Mitsui Toatsu Chemicals, Inc., Tokyo, Japan

[21] Appl. No.: 274,453

[22] Filed: Jul. 13, 1994

[30] Foreign Application Priority Data

Jul. 23, 1993 [JP] Japan .................................. 5-182987
Sep. 28, 1993 [JP] Japan .................................. 5-241039

[51] Int. Cl.$^6$ ..................... C08L 77/00; C08L 23/26; C07C 231/06
[52] U.S. Cl. ..................... 523/310; 558/464; 564/126; 564/127; 564/128; 564/206
[58] Field of Search .................... 558/464; 564/126, 564/127, 128, 206; 523/310

[56] References Cited

U.S. PATENT DOCUMENTS

| | | | |
|---|---|---|---|
| 2,444,589 | 7/1948 | Blann | 260/465.6 |
| 2,622,097 | 12/1952 | Osborne | 260/465.9 |
| 3,923,741 | 12/1975 | Asano et al. | 564/127 |
| 3,941,837 | 3/1976 | Asano et al. | 564/127 |
| 3,951,600 | 4/1976 | Asano et al. | 564/127 |
| 3,962,333 | 6/1976 | Yoshimura et al. | 564/127 |
| 4,177,210 | 12/1979 | Vanderkooi et al. | 260/561 N |
| 4,188,339 | 2/1980 | Yamaguchi et al. | 564/128 |
| 4,302,600 | 11/1981 | Saitoh et al. | 564/206 |
| 4,313,001 | 1/1982 | Itoh et al. | 564/206 |
| 4,345,101 | 8/1982 | Asano et al. | 564/206 |

FOREIGN PATENT DOCUMENTS

| | | |
|---|---|---|
| 55-157543 | 12/1980 | Japan . |
| 56-133250 | 10/1981 | Japan . |
| 2114118 | 8/1983 | United Kingdom . |

OTHER PUBLICATIONS

Chemical Abstracts, vol. 96, No. 10, Mar. 8, 1982.

Primary Examiner—John C. Bleutge
Assistant Examiner—Randy Gulakowski
Attorney, Agent, or Firm—Burns, Doane, Swecker & Mathis

[57] ABSTRACT

This invention provides a process for the preparation of acrylamide. Acrylonitrile is treated through at least two purification steps in which acrylonitrile is brought into contact with a strongly-acidic cation exchange resin and then with a resin having primary and/or secondary amino groups or with activated carbon. The resulting acrylonitrile is subjected to hydration in the presence of a copper-base catalyst. The process of this invention can provide high-quality acrylamide even when acrylonitrile of ordinary quality is used, and permits preparation of a polyacrylamide suitable for use in the production of a coagulant having good water solubility or the like.

7 Claims, No Drawings

PREPARATION PROCESS OF ACRYLAMIDE FROM PURIFIED ACRYLONITRILE

BACKGROUND OF THE INVENTION a) Field of the Invention

This invention relates to a process for preparing acrylamide by subjecting acrylonitrile to catalytic hydration with water in the presence of a copper-base catalyst. More specifically, this invention is concerned with a purification process for acrylonitrile useful as a raw material for the preparation of high-quality acrylamide which permits production of a polymer having sufficiently high molecular weight and also good water-solubility.

b) Description of the Related Art

Acrylamide has long been used in the form of acrylamide polymers as papermaking chemicals, flocculants, oil recovery agents and the like and has also found wide-spread utility as a raw material comonomer for various polymers. As a preparation process of acrylamide for such applications, the so-called sulfuric acid process was used in the past but in recent years, catalytic processes featuring a reaction in the presence of a copper-base catalyst have been developed and are now industrially practiced in place of the sulfuric process.

Among the above-described applications of acrylamide, flocculants in particular have found utility expanded to the treatment of effluent and the like in recent years. Keeping step with this, a great deal of efforts are now under way for the improvement of their quality and performance. Of these, there is a marked tendency toward high-molecular acrylamide polymers for use as flocculants because they are said to exhibit better performance as their molecular weights become higher. Recently, those having a high molecular weight of 10,000,000 or higher, especially of about 15,000,000 are demanded. Compared with the fact that the molecular weight required for an acrylamide polymer or other polymers employed for other applications is generally 1,000,000 or lower, this molecular weight is far higher. In addition, the acrylamide polymer so obtained is required to promptly dissolve in water without leaving any insoluble matter behind because it is usually employed as a flocculant in a form dissolved in water. In view of the toxicity of acrylamide monomer, the unreacted monomer contained in each polymer is required to be in a trace amount, for example, not greater than 0.2 wt. %.

These requirements are contradictory to the demand for higher molecular weight so that tremendous efforts have been made to achieve them. Although such high-molecular acrylamide polymers constitute only one example of applications of acrylamide, they cannot be furnished for a wide variety of general applications unless they are suited for application as flocculants. A process according to the present invention relates to the preparation of acrylamide which can be furnished for such an application.

The term "molecular weight" as used herein means a molecular weight determined by the testing method shown in Example 1 which will be described subsequently herein. Water solubility takes significance usually when a polymer obtained in an aqueous medium is dried into dry powder having a water content of 20 wt. % or lower, especially 10 wt. % or so. The term "water solubility" as used herein is primarily employed in this sense.

To produce an acrylamide polymer having such high molecular weight and sufficient water solubility as described above, it is considered important to pay attention not only to a process for the production of the polymer but also to the quality of acrylamide. Further, the quality of acrylonitrile as the raw material is also considered to significantly affect the production of such an acrylamide polymer.

Acrylonitrile is usually synthesized by ammoxydation of propylene. Acrylic fibers and ABS resin account for a majority of applications of acrylonitrile. Acrylonitrile, which is employed as a raw material for the production of acrylamide by the catalytic hydration process, is required to have higher quality so that it contains less impurities than that employed for such major applications. To meet this requirement, it is the common practice to take a measure such as making operation conditions for a distilling purification step severer.

To make acrylonitrile suitable for the catalytic hydration process, several methods have been proposed.

According to Japanese Patent Laid-Open No. 118305/1988 (corresponding to U.S. Pat. No. 4,177,210), for example, acrylonitrile as a raw material is brought into contact with an H-type cation exchange resin to lower the content of oxazole to 200 ppm or less, more preferably to 25 ppm or less in the acrylonitrile. This publication also discloses that acrylamide, which has been synthesized by subjecting the acrylonitrile to hydration in the presence of a copper-base catalyst, has higher stability and when polymerized, provides an aqueous solution of higher viscosity compared with acrylamide synthesized likewise from oxazole-containing acrylonitrile. It is also disclosed that as a method for the regeneration of the cation exchange resin, the cation exchange resin is brought into contact with hot water, water vapor, methanol, a slightly-acidic aqueous solution or a mixture thereof.

Japanese Patent Publication No. 26264/1982 discloses that when acrylonitrile is purified by an inorganic acid or an acidic cation exchange resin, the acrylonitrile can avoid deterioration of the catalytic activity compared with unpurified acrylonitrile in hydration reaction in the presence of a copper-base catalyst.

Japanese Patent Publication No. 26586/1982 discloses that when the concentration of acrolein in acrylonitrile is reduced to 1.5 ppm or less, more preferably 0.8 ppm or less by reacting the acrolein with acetylacetone or the like and then by isolating the reaction product and the acrylonitrile from each other by distillation or the like, acrylamide obtained by subjecting the acrylonitrile to hydration in the presence of a copper-base catalyst can provide a polymer having good water solubility.

Japanese Patent Publication No. 1108/1983 discloses that acrylamide—which has been obtained by lowering the content of acrolein to 0.8 ppm or less in acrylonitrile by bringing the acrylonitrile into contact with a porous ion exchange resin having primary and/or secondary amino groups as exchanging groups and then subjecting the resultant acrylonitrile to hydration in the presence of a copper-base catalyst—can provide a polymer having good water solubility and sufficiently high molecular weight.

Similarly, Japanese Patent Laid-Open No. 134063/1983 discloses that when the content of aldehydes, practically acrolein in acrylonitrile is reduced by bringing the acrylonitrile into contact with a gel-type, weakly-basic ion exchange resin containing primary and/or secondary amino groups, the acrylonitrile can form acrylamide capable of providing a polymer having improved water-solubility and also that when acrylamide itself is treated in a similar manner, the acrylamide so treated can provide a polymer having improved water-solubility and sufficiently high molecular weight.

According to Japanese Patent Publication No. 9303/1986, acrylonitrile is subjected to water extraction and/or to water extraction and distillation to lower the content of acetonitrile to 20 ppm or less, more preferably 10 ppm or less and is then subjected to hydration at a temperature of 100°–140° C. in the presence of a copper-base catalyst. It is disclosed that this acrylamide can provide a polymer having improved water solubility.

Further, U.S. Pat. No. 2,444,589 issued in 1948 points out that acrylonitrile synthesized from an inorganic cyanide and an organic substance contains trace amounts of ionic impurities and trace amounts of neutral impurities and these impurities hamper isolation of a synthetic reaction product from acrylonitrile as a raw material and lower its yield. It is also disclosed that when this acrylonitrile is treated with a cation exchange material (for example, a phenylformaldehyde condensation product, sulfonated coal or the like) and an anion exchange resin (for example, a condensation product of guanidine, urea or formaldehyde) to remove ionic substances and is then treated with a decoloring agent (for example, activated carbon), decoloration not feasible by single use of the ion exchange materials or the decoloring agent is feasible. Further, it is also disclosed in one of its examples that acrylonitrile—which has been treated successively with a cation exchange resin, an anion exchange resin and activated carbon in the order that they are presented—provides a high polymerization velocity.

According to a finding of the present inventors, the quality of acrylamide obtained by subjecting acrylonitrile to catalytic hydration with water in the presence of a copper-base catalyst cannot provide an acrylamide polymer sufficient in water solubility and molecular weight when polymerized singly or with another comonomer, even if oxazole, acrolein, acetonitrile and the like in the acrylonitrile are eliminated by using the above-described art.

The process commonly practiced these days, in which operation conditions for the distillation-dependent purification step are made severer to prepare low-impurity acrylonitrile for use as a raw material for the preparation of acrylamide, involves considerable sacrifices of a recovery loss in the distillation-dependent purification step and increased consumption of energy such as steam. Although use of so-obtained low-impurity acrylonitrile in catalytic hydration generally leads to acrylamide of good quality, the product may be obtained with insufficient quality in some instances. Accordingly the process is insufficient in the stability of quality and is insufficient as a commercial preparation process for high-quality acrylamide.

At the time of the issuance of U.S. Pat. No. 2,444,589 in 1948, said U.S. patent containing the above-mentioned example directed to the use of the cation exchange resin, the anion exchange resin and activated carbon, neither (a) a preparation process of acrylonitrile by ammoxydation of propylene nor (b) a preparation process of acrylamide by hydration of acrylonitrile in the presence of a copper-base catalyst had been practiced industrially. This U.S. patent does not contain any disclosure about (c) purification of acrylonitrile prepared by ammoxydation of propylene by the process of the patent or (d) effects of acrylamide, which was obtained by catalytic hydration of acrylonitrile (c) with water in the presence of the copperbase catalyst, on an acrylamide polymer obtained by polymerizing the acrylamide singly or with another comonomer. Further, neither the purification (c) nor the effects (d) have been known to date.

Although in the above-mentioned example, acrylonitrile was treated with the cation exchange resin, the anion exchange resin and activated carbon in the order that they are presented, what is disclosed in this patent is to easily eliminate neutral impurities as a cause for coloration or the like by removing ionic substances. In other words, it is only necessary to perform the cation exchange treatment and the anion exchange treatment prior to the treatment with the decoloring agent (for example, activated carbon). The above U.S. patent does not specify the order of the cation exchange treatment and the anion exchange treatment in the ion exchange treatment.

SUMMARY OF THE INVENTION

The present inventors have proceeded with an extensive investigation on a purification process of acrylonitrile as a raw material for the preparation of acrylamide with a view toward providing an acrylamide polymer having sufficient water solubility and molecular weight by polymerization of the acrylamide, leading to the present invention.

The above object of the present invention can be achieved by the provision of a process for the preparation of acrylamide, which comprises bringing acrylonitrile into contact with at least a strongly-acidic cation exchange resin and then with a resin having primary and/or secondary amino groups or with activated carbon, and thereafter subjecting the resultant acrylonitrile to hydration in the presence of a copper-base catalyst.

In one specific aspect of the present invention, there is provided a process which comprises treating acrylonitrile in two steps, that is, bringing acrylonitrile into contact with at least a strongly-acidic cation exchange resin and then with a resin having primary and/or secondary amino groups, and thereafter subjecting the resultant acrylonitrile to hydration in the presence of a copper-base catalyst. In another aspect of the present invention, there is also provided a process which comprises treating acrylonitrile in two steps, that is, bringing acrylonitrile into contact with at least a strongly-acidic cation exchange resin and then with activated carbon, and thereafter subjecting the resultant acrylonitrile to hydration in the presence of a copper-base catalyst.

In the present invention, the acrylonitrile can preferably be that prepared by ammoxydation of propylene. After acrylonitrile has been brought into contact with the strongly-acidic cation exchange resin, the acrylonitrile can preferably be brought into contact first with the resin having primary and/or secondary amino groups and then with activated carbon. After acrylonitrile has been brought into contact with the resin having primary and/or secondary amino groups, the acrylonitrile can desirably be brought into contact first with the strongly-acidic cation exchange resin and then with activated carbon. As a further preferred alternative, after acrylonitrile is brought into contact with the strongly-acidic cation exchange resin, the acrylonitrile can be brought into contact first with activated carbon and then with the resin having primary and/or secondary amino groups.

DETAILED DESCRIPTION OF THE INVENTION

The term "process for the preparation of acrylonitrile by ammoxydation of propylene" as a preferred embodiment in the present invention means a preparation process by vapor-phase catalytic ammoxydation in which a gaseous mixture of propylene, ammonia, and oxygen or air is directly reacted in the presence of a catalyst such as a molybdenum-bismuth catalyst, a uranium-antimony catalyst or an iron-antimony catalyst.

Acrylonitrile is generally recovered by absorbing it in water from a synthetic reaction gas and in a subsequent purification and isolation step, is separated from byproducts such as prussic acid, acetonitrile, acetone, acrolein, methacrylonitrile, oxazole and aldehydes. Distillation is primarily used for the purification and isolation. When acrylonitrile is prepared as a raw material for acrylamide, however, it is commonly practiced to make conditions for the distillation and purification severer so that impurities can be reduced.

Application of the present invention, however, makes it possible to provide acrylonitrile of ordinary quality as a raw material for acryl fibers.

A preparation process for acrylamide, to which the present invention can be applied, will next be described in short.

Examples of the copper-base catalyst used in the process of the present invention include:

(A) a combination of copper in the form of copper wire or copper powder with copper ions;

(B) a copper-base catalyst (reduced copper) by reducing a copper compound with a reducing agent;

(C) a copper-base catalyst (copper as a decomposition product) obtained by decomposing a copper compound with heat or the like; and (D) a copper-base catalyst (Raney copper) obtained by dissolving the aluminum out of a Raney alloy with an alkali or the like.

Examples of a process for the production of reduced copper include:

(1) reduction of copper oxide with hydrogen, carbon monoxide or ammonia in a gas phase;

(2) reduction of a copper salt or copper hydroxide with formaldehyde, hydrazine or sodium borohydride in an aqueous solution; and (3) reduction of a copper salt or copper hydroxide with elemental aluminum, zinc or iron in an aqueous solution.

In each of these processes, a principal catalytic component of the reduction product is considered to be elemental copper.

Examples of a process for the production of copper as a decomposition production include:

(1) thermal decomposition of copper hydride, which has been obtained by treating a copper compound with sodium hypochlorite, in an aqueous alkali solution;

(2) thermal decomposition of copper formate or copper oxalate;

(3) thermal decomposition of so-called cluster copper disclosed in Japanese Patent Laid-Open No. 108015/1974; and (4) direct addition of copper acetylide or copper nitride to a hydration reaction system of acrylonitrile.

In each of these processes including the process (4), a principal catalytic component of the decomposition product is considered to be elemental copper.

Examples of a process for the production of Raney copper include:

(1) substantially complete dissolution of the aluminum out of a copper-aluminum alloy with caustic soda, sulfuric acid, water, an organic amine or the like; and (2) partial dissolution of the aluminum out of a copper-aluminum alloy with caustic soda, sulfuric acid, water, an organic amine or the like, so that the aluminum is partly allowed to remain together with the copper.

In each of these processes, a principal catalytic component of the dissolution product is considered to be elemental copper.

These copper-base catalysts can be used in a form borne on a conventionally employed carrier. They can also contain a metal other than copper, for example, chromium or molybdenum.

Although the above-described copper-base catalysts vary in catalytic activity itself depending on the production processes, the manner of reaction such as side reactions does not differ whichever copper-base catalyst is employed, for example, among reduced copper, copper hydride, Raney copper and the like. The copper-base catalysts have the same trend with respect to the production of impurities.

It is desired to avoid contact of the catalyst with oxygen or an oxygen-containing gas both before and after its use, because oxygen deprives the copper-base catalyst of catalytic activity and increases byproducts such as ethylene cyanhydrin.

The hydration of acrylonitrile according to the present invention is carried out in the presence of the copper-base catalyst as will be described next. The reaction is carried out continuously or batchwise in a liquid phase while using the catalyst in the form of a suspended or fixed bed.

The weight ratio of acrylonitrile to water, both to be subjected to hydration, can be determined practically as desired. The preferred weight ratio may be in a range of from 60:40 to 5:95, with a range of from 50:50 to 10:90 being more preferred. The preferred conversion of acrylonitrile may be from 10% to 98%, with a range of from 30% to 95% being more preferred.

The reaction temperature in the hydration of acrylonitrile with water may preferably range from 50° C. to 200° C., with a range of from 70° C. to 150° C. being more preferred.

The interior of a reactor is maintained under a pressure, which is the vapor pressure of the reactants at the above-described temperature and composition or where an inert gas such as nitrogen is charged, the sum of the vapor pressure and the pressure of the inert gas. This pressure generally ranges from normal pressure to 10 atm. Oxygen which may generally be contained in a dissolved form in the catalyst, acrylonitrile, water and the like, all to be fed to the reactor, impairs the activity of the catalyst and increases byproducts such as ethylene cyanhydrin. It is therefore desired to fully eliminate such oxygen before feeding them to the reactor. For the same reasons, it is also desired to maintain the interior of the reactor under an oxygen-free atmosphere. The liquid reaction mixture to be taken out of the reactor subsequent to the hydration is composed primarily of unreacted acrylonitrile, unreacted water and acrylamide and also contains byproducts such as ethylene cyanhydrin together with copper.

The liquid reaction mixture obtained through the above reaction can be subjected, if desired, to usual evaporation or distillation, thereby obtaining a concentrated aqueous solution of acrylamide and recovering unreacted acrylonitrile and water as distillates. These recovered materials can be used again as fresh reaction raw materials.

The content of impurities and the like in acrylonitrile as described herein means their content in freshly supplied acrylonitrile and is not their content in the mixture of acrylonitrile freshly supplied and acrylonitrile recovered and reused.

The aqueous acrylamide solution, which has been obtained by concentrating the liquid reaction mixture and will hereinafter be called simply the "aqueous acrylamide solution", is then purified by various purification methods such as cation exchange treatment, chelate resin treatment, anion exchange treatment, air or oxygen gas treatment, and activated carbon treatment. As an alternative, a so-called synthetic adsorbent resin (for example, "Adsorbent Resin", trade name, product of Hokuetsu Carbon Industry Co., Ltd.) employed in a similar manner to activated carbon or ion exchange resins can also be used. In the course of or subsequent to the above purification step, the aqueous acrylamide solution can be subjected to the above concentration treatment or can be reconcentrated.

Next, the purification process of acrylonitrile will be described in detail.

The strongly acidic cation exchange resin (a) employed for the purification of acrylonitrile may be a gel-type resin such as "Levatit S-100" (trade name; product of Bayer AG), "Diaion SK1B" (trade name; product of Mitsubishi Kasei Corp.) or "Dowex HCR-W2" (trade name; product of Dow Chemical Co.) or a macroporous resin such as "Levatit SP-112" (trade name; product of Bayer AG) or "Dowex MSC-1" (trade name; product of Dow Chemical Co.). Although such a resin can be used by pretreating it with a dilute acid to convert it to an H-form, and then thoroughly washing it with water, it is more desired to use the resin after fully drying it with hot air or dry nitrogen or under reduced pressure.

When the resin containing primary and/or secondary amino groups is employed, it is necessary to contain either primary amino groups or secondary amino groups or both. For example, either a porous resin such as "Diaion WA-20" (trade name; product of Mitsubishi Kasei Corp.) or a gel-type resin such as "Levatit OC1059" (trade name; product of Bayer AG) can be used. A commercial product can be used after it is thoroughly washed with water. It is of course possible to use a commercial product by treating it with a dilute alkali solution and then thoroughly washing the same. Further, irrespective of whether the pretreatment with the dilute alkali solution is conducted or not, the water-washed resin can be used after fully drying it with hot air or dry nitrogen or under reduced pressure.

When brought into contact with activated carbon, no particular limitation is imposed on the type of activated carbon. Usable examples include coal-base activated carbon such as "Calgon CPG" (trade name; product of Calgon Corp.) and coconut-shell-base activated carbon such as "Shirasagi LHc" (trade name; product of Takeda Chemical Industries, Ltd.). These commercial activated carbon can be used as are. Needless to say, they can be use after washing them with water or then fully drying them with hot air or dry nitrogen or under reduced pressure.

These resins and activated carbon can each be used by packing it as a fixed bed in a column or the like and then continuously bringing acrylonitrile into contact with it for purification. They can also be used in batchwise treatment. The former is however desired for the efficiency of purification, the readiness of operation and the like.

According to the present invention, it is essential to bring acrylonitrile into contact with the strongly-acidic cation exchange resin (a) upon purification of acrylonitrile. In addition, the acrylonitrile is also brought into contact with (b) the resin containing primary and/or secondary amino groups and/or (c) activated carbon. The order of these contacts can be:

1) (a)→(b),
2) (a)→(c),
3) (a)→(b)→(c),
4) (b)→(a)→(c), or
5) (a)→(c)→(b).

They all fall within the breadth of the present invention. Upon conducting the purification treatment in any one of the orders 1) to 5), acrylonitrile can be beforehand brought into contact with activated carbon (c) for purification. This practice also falls within the breadth of the present invention.

When these resins and activated carbon are used in a form packed in columns, these columns should be made of a material resistant to acrylonitrile, for example, SUS-304 or the like.

Upon treatment of acrylonitrile through these columns, the temperature of acrylonitrile may generally be 5°–50° C., with 15°–30° C. being preferred. The flow rate of acrylonitrile through each column can be chosen from flow rates of 0.1–50 times per hour, preferably about 0.5–10 times per hour, both relative to the volume of a resin or activated carbon packed in the column.

Where flow-out of a basic substance typified by oxazole, for example, is detected in the course of contact of acrylonitrile with the strongly-acidic cation exchange resin (a), the resin (a) can be easily regenerated by bringing water of room temperature to 100° C., water vapor, methanol, a dilute acid or a mixture thereof into contact with the resin.

Using purified acrylonitrile obtained as described above, the preparation of acrylamide was conducted by subjecting it to catalytic hydration with water in the presence of the copper-base catalyst. This acrylamide was then polymerized either singly or in combination with another monomer to provide an acrylamide polymer. The acrylamide polymer was found to have far-improved water solubility and sufficiently high molecular weight.

Purification processes other than the above ones 1) to 5), for example, i) purification of acrylonitrile only by the strongly-acidic cation exchange resin (a), ii) purification of acrylonitrile only by the resin containing primary and/or secondary amino groups, iii) purification of acrylonitrile only by activated carbon, and iv) a process including as a last step contact to the strongly-acidic cation exchange resin (a), for example, (b)→(a), (b)→(c)→(a), etc.

were conducted in a manner similar to the above-described purification processes. Confirmed through analysis were the elimination of oxazole in the treatment i), the elimination of acrolein in the treatment ii), and the elimination of both oxazole and acrolein in the treatment iv).

Whichever purified acrylonitrile was used for the preparation of acrylamide by the above-described catalytic hydration with water in the presence of the copper-base catalyst, the resulting acrylamide was unable to provide an acrylamide polymer having satisfactory water solubility when polymerized either singly or in combination with another comonomer.

The following explanation can probably be made in this respect. The treatment i) was able to eliminate only oxazole while the treatment ii) was able to eliminate only acrolein. Accordingly the acrylonitrile samples obtained by the treatments i) and ii), respectively, were not believed to have sufficient purity. The acrylamide sample obtained by the treatment iv), in which both oxazole and acrolein have been eliminated, was also found ineffective in providing acrylamide of improved quality. As a reason for this, the treatment with the strongly-acidic cation exchange resin (a) as a last step would conversely lead to an increase in the content of impurities other than acrolein, such as aldehydes, and would hence unable to provide acrylamide of improved quality.

Among the processes 1) to 5), the process 3) in which acrylonitrile is brought into contact with (a) the strongly-acidic cation exchange resin, (b) the resin containing primary and/or secondary amino groups and (c) activated carbon in the order that they are presented can bring about the best results, namely, can provide acrylamide of high quality.

Although the reason for this has not been fully elucidated, the effects of purification of acrylonitrile according to the present invention have been brought about not only for the elimination of impurities independently by the strongly-acidic cation exchange resin, the resin containing primary and/or secondary amino groups and activated carbon but also for the elimination of certain specific undesired impurities by combined or synergistic action of (a) the strongly-acidic cation exchange resin, (b) the resin containing primary and/or secondary amino groups and (c) activated carbon in the order that they are presented.

A process for the production of a high-molecular acrylamide polymer useful as a flocculant will next be described in brief.

Acrylamide is used either singly or in combination with a copolymerizable vinyl comonomer. Examples of the comonomer include acrylic acid, methacrylic acid and water-soluble salts thereof; alkylaminoalkyl acrylates and methacrylates, and their quaternary ammonium derivatives; N-(dimethylaminopropyl)methacrylamide and its quaternary ammonium derivative; vinyl acetate; and acrylonitrile. As the mixing ratio of such a comonomer with acrylamide, the comonomer can be used generally in an amount of 100 moles or less, especially 50 moles or less per 100 moles of acrylamide.

The polymerization between acrylamide and the comonomer is conducted by a method known per se in the art such as aqueous solution polymerization or emulsion polymerization. A description will next be made of a general process of aqueous solution polymerization which is most widely employed.

The total concentration of acrylamide and the comonomer is generally set at 5–60 wt. %. Usable examples of a polymerization initiator include peroxides such as potassium persulfate, ammonium persulfate, hydrogen peroxide and benzoyl peroxide; free azo radical initiators such as azobisisobutyronitrile, 2,2'-azobis(4-amidinopropane) dihydrochloride and sodium 4,4'-azobis(4-cyanovalerianate); and so-called redox catalysts such as combinations of the above-described peroxides with reducing agents such as sodium bisulfite, triethanolamine and ferrous ammonium sulfate.

Regarding the temperature of the polymerization reaction, adiabatic polymerization is usually adopted where the total concentration of acrylamide and the comonomer is 15 wt. % or higher and the resulting polymer has a molecular weight as high as 10,000,000 or greater, because it is difficult to control the temperature by cooling or the like. In this case, the temperature of the reaction system arises due to the heat of polymerization as the polymerization proceeds. In this instance, the temperature at the time of initiation of the polymerization is often selected from a range of from $-5°$ C. to $40°$ C. and upon completion of the reaction, the temperature reaches a temperature as high as $55°$ C. to $100°$ C., for example.

To provide a molecular weight of 10,000,000 or higher, notably a high molecular weight of approximately 15,000,000, the total concentration of acrylamide and the comonomer, the kind and concentration of the polymerization initiator to be employed, the reaction temperature and the like are contrived. A similar ingenious measure is also taken to lower the content of unreacted acrylamide to a trace amount, for example, 0.2 wt. % or below. Especially, many processes featuring two or more kinds of polymerization initiators caused to act in different temperature ranges have been proposed and practiced.

The polyacrylamide obtained by such a polymerization reaction as described above is in the form of a water-containing gel, that is, a rubbery gel which contains substantially all the water employed to form acrylamide and the comonomer into an aqueous solution. To convert it into a dry powder-like product, the polyacrylamide is usually subjected to further processing such as dewatering by extraction of water or drying under heat or crushing or grinding in the form of either the water-containing gel or dried gel. Prior to or in the course of these processing, the acrylamide polymer can be chemically modified by kneading caustic soda in the water-containing gel and heating the resultant mass to convert some amido groups into carboxyl groups.

As a result of an increase in molecular weight, a reduction in unreacted monomers, formation into dry powder and in some instances, a chemical modification as described above, the resulting polymer is often hardly soluble in water and tends to lose its value as a commercial product such as a coagulant. With a view toward overcoming this problem, it is practiced to add an insolubilization preventive before, during or after the polymerization reaction, to use a special polymerization initiator or to conduct the drying of water-containing gel under specific conditions.

Acrylamide to which the process of the present application is applied is prepared in accordance with a process which as generally described above, comprises purification of acrylonitrile, hydration, distillation, various purification treatments and other additional steps, and is used for the production of an acrylamide polymer having a high molecular weight as also described above in general.

The present invention will next be described in further detail by the following examples.

Example 1

<Purification of acrylonitrile>

One liter of a strongly-acidic cation exchange resin ("Levatit S-100", trade name; product of Bayer AG), which had been treated with dilute hydrochloric acid into an H-form and then thoroughly washed with water in a usual manner, was dried at $90°$ C. under normal pressure for about 8 hours and was then packed in a column having an internal diameter of 70 mm and a length of 400 mm and made of SUS-304. One liter of a resin containing primary and/or secondary amino groups ("Diaion WA-20", trade name; product of Mitsubishi Chemical Corp.) was washed with water and then packed in a column having an internal diameter of 70 mm and a length of 400 mm and made of SUS-304. One liter of an activated carbon ("Calgon CPG", trade name; product of Calgon Corp.) was washed with water and then packed likewise in a column having an internal diameter of 70 mm and a length of 400 mm and made of SUS-304.

Those three columns were connected together in the order of "Levatit S-100" as a first column, "Diaion WA-20" as a second column and "Calgon CPG" as a third column. Acrylonitrile, which had been prepared by ammoxydation of propylene, was then caused to pass through those columns at a flow rate of 6 l/hr. The concentrations of impurities in the acrylonitrile (LOT 1) employed as the raw material are presented in Table 1. As will be understood from the concentrations, the acrylonitrile was of ordinary quality useful in the production of acrylic fibers and the like. The concentrations of impurities of purified acrylonitrile after treated through the columns are also shown in Table 1.

<Preparation of acrylamide>

Using the purified acrylonitrile prepared by the above-described method, acrylamide was obtained by subjecting the purified acrylonitrile to hydration in the presence of a copper-base catalyst as will be described next.

Catalyst for the hydration:

Using caustic soda, the aluminum was dissolved out of a Raney copper alloy not greater than 80 mesh in a manner known per se in the art, followed by washing to product a Raney copper catalyst. During the production and upon subsequent handling, the catalyst was kept out of contact with any oxygen-containing gas such as air.

Catalytic hydration:

A reactor made of SUS, internally equipped with a stirrer and a catalyst separator and having a capacity of about 2 l was charged with 400 g of the above-described catalyst. Acrylonitrile and water, from which dissolved oxygen had been eliminated beforehand by nitrogen gas, were fed at velocities of 600 g/hr and 900 g/hr, respectively, and were reacted at 120° C. The liquid reaction mixture was stirred together with the catalyst into a suspension. The suspension was then passed through a catalyst separator and the resulting solution practically free of the catalyst was taken out of the reactor. That reaction was continued for 3 days.

Concentration:

The liquid reaction mixture so obtained was subjected batchwise to concentration under reduced pressure to distillate unreacted acrylonitrile in toto and unreacted water in part, whereby an aqueous acrylamide solution having a concentration of about 50 wt. % was obtained. The aqueous acrylamide solution contained copper.

Decoppering treatment:

A glass-made column was packed with 150 ml of the strongly-acidic cation exchange resin ("Levatit SP-112", trade name; product of Bayer AG) which had been pretreated with dilute hydrochloric acid into an H-form. The aqueous acrylamide solution obtained by the above-described concentration treatment was caused to pass at 900 ml/hr through the column. The copper content and pH of the resulting solution were 0.01 ppm or below and 3.5–4.0, respectively.

pH regulation:

Caustic soda was continuously added during the decoppering treatment, so that the pH of the solution under the decoppering treatment was maintained at about pH 6.5.

<Production process of acrylamide polymer>

The aqueous acrylamide solution obtained in the above-described manner was polymerized in the following manner, whereby an acrylamide polymer was obtained.

Water was added to the aqueous acrylamide solution to adjust the concentration to 20 wt. %. A 500 g portion of the solution was placed in a 1-l polyethylene vessel and while maintaining the solution at 18° C., the solution was sparged with nitrogen gas to eliminate dissolved oxygen in the solution. The solution was immediately placed in a heat-insulating block made of styrene foam.

To the solution, $200 \times 10^{-6}$ mpm (molar ratio to acrylamide) of sodium 4,4'-azobis(4-cyanovalerianate), $200 \times 10^{-6}$ mpm of dimethylaminopropionitrile and $80 \times 10^{-6}$ mpm of ammonium persulfate, which had been separately dissolved in small amounts of water, were poured quickly in the order that they are presented. Those reagents had been sparged with nitrogen gas in advance and further, the above polyethylene vessel was also purged with a small amount of nitrogen gas during and before and after the pouring, so that mixing of oxygen gas was prevented. After an induction period of several minutes subsequent to the pouring of the reagents, the internal temperature of the polyethylene vessel was observed to rise. The feeding of nitrogen gas was therefore stopped. After the temperature reached a maximum temperature of about 70° C. approximately 100 minutes later, the polyethylene vessel was taken out of the insulating block, immersed for 2 hours in water of 97° C., and then dipped in chilled water to cool it down.

The acrylamide polymer obtained above in the form of a water-containing gel was divided into small pieces, ground through a mincer, dried for 2 hours in hot air of 100° C. and then ground in a high-speed rotary blade grinder, so that the acrylamide polymer was obtained in the form of dry powder. The dry powder was sifted through sieves to collect powder of 32–42 mesh as a polymer sample to be tested subsequently. The water content of the polymer sample was determined as a weight loss upon overnight hot air drying at 125° C. Each polymer sample was found to have a water content of about 10 wt. %.

<Testing methods of acrylamide polymer>

The water solubility and standard viscosity of each polymer sample obtained in the above-described manner were determined by the following methods.

Water solubility:

Six hundred milliliters of water were placed in a 1-l beaker and while stirring the water by a stirring blade of a predetermined shape, 0.66 g (0.6 g in a pure form) of the polymer sample was added, followed by stirring at 400 rpm for 2 hours. The resulting solution was filtered through a 150 mesh wire screen. The water solubility of the polymer sample was determined from the amount of insoluble matter and the filter-ability. The water solubility of each polymer sample was ranked according to the following standard:

A—Completely dissolved.

B—Almost completely dissolved.

C—Insoluble matter was contained but was filterable.

D—Filtration of the solution was slow so that filtration of insoluble matter was practically impossible.

Where polyacrylamide has a molecular weight of about 15,000,000 or higher and its water solubility is ranked as "B", the polyacrylamide is considered to have quality sufficient for use as a flocculant. Where the water solubility is ranked "C", the polyacrylamide can be used as a papermaking reagent but can hardly be employed as a flocculant. If the water solubility is D, the polyacrylamide is not suited for use in most applications and does not have commercial value.

Molecular weight:

To determine the molecular weight of each acrylamide polymer, aqueous polyacrylamide polymer solutions of different concentrations were prepared by using a filtrate obtained by similar procedures to those employed above for the determination of water solubility. The solutions were then added with an aqueous solution of sodium nitrate to a concentration equivalent to 1M. Using a capillary viscometer, the intrinsic viscosity was determined. The molecular weight of the acrylamide polymer was calculated in accordance with the following formula:

$$\text{Intrinsic viscosity} = 3.73 \times 10^{-4} \times [\text{weight average molecular weight}]^{0.66}$$

Incidentally, each filtrate obtained in the above water solubility test was a 0.1 wt. % aqueous polymer solution where the water solubility is good. The aqueous polymer solution was added with sodium chloride to a concentration equivalent to 1M. By a BL-type viscometer equipped with a BL adapter, the viscosity (standard viscosity) of the resulting solution was measured at 25° C. and a rotor revolution speed of 60 rpm. Since the standard viscosity obtained in the manner described above is commonly employed as a value relevant to the molecular weight, it is also used in combination with others in the present example. The results of an evaluation conducted by the above-described methods are summarized in Table 1. The water solubility of the resultant polymer was ranked as "A" and its standard viscosity was 5.7 cps (molecular weight: about 15,800,000). The polyacrylamide therefore had good quality.

Comparative Example 1

The procedures of Example 1 were repeated except for the omission of the purification of acrylonitrile. The water solubility of the resultant polyacrylamide was ranked as "D" and its viscosity was unmeasurable. The polyacrylamide therefore did not have commercial value.

Based on Example 1 and Comparative Example 1, it has been found that the application of the present invention to acrylonitrile of ordinary quality, which has heretofore been unusable as a raw material for acrylamide, makes it possible to prepare acrylamide of high quality sufficient for use in the production of a flocculant.

EXAMPLE 2

Using acrylonitrile (LOT-2) which had been subjected to severer distillation and purification than ordinary product to lower the contents of impurities and was of the same quality as that commonly employed as a raw material for acrylamide, acrylamide was prepared in a similar manner to Example 1. The results are presented in Table 1. The polymer so obtained had very good quality, that is, its water solubility was ranked as "A" and its standard viscosity was calculated as 5.9 cps (molecular weight: about 16,700,000).

Comparative Example 2

The procedures of Example 2 were repeated except for the omission of the purification of acrylonitrile. The results are presented in Table 2. The polymer so obtained had lowest quality acceptable as a flocculant because its water solubility was ranked as "B" and its standard viscosity was calculated as 5.6 cps (molecular weight: about 15,300,000).

Based on Example 2 and Comparative Example 2, it has been found that the application of the present invention to acrylonitrile of low impurity level as a raw material for acrylamide will result in the provision of a polyacrylamide having extremely improved quality.

EXAMPLE 3

Procedures similar to Example 1 were conducted except that upon purification of acrylonitrile (LOT-1), the order of the purification columns was changed to arrange "Diaion WA-20" as a first column, "Levatit S-100" as a second column and "Calgon CPG" as a third column. The results are presented in Table 2. Although the polyacrylamide obtained from the unpurified acrylonitrile in Comparative Example 1 did not have any commercial value, the application of the present invention resulted in a polyacrylamide having quality sufficient for use as a papermaking reagent as indicated by the water solubility ("C") and the standard viscosity (5.7 cps).

EXAMPLE 4

The procedures of Example 3 were repeated except for the use of LOT-2 as acrylonitrile in lieu of LOT-1. The results are presented in Table 2. The resultant polyacrylamide had quality substantially improved over that obtained in Comparative Example 2, as indicated by its water solubility ("A") and its standard viscosity (5.8 cps; molecular weight: about 16,200,000).

EXAMPLE 5

Procedures similar to Example 1 were conducted except that the order of the purification columns was changed to arrange "Levatit S-100" as a first column, "Calgon CPG" as a second column and "Diaion WA-20" as a third column. The results are presented in Table 2. Although the polyacrylamide obtained from the unpurified acrylonitrile in Comparative Example 1 did not have any commercial value, the application of the present invention resulted in a polyacrylamide having quality sufficient for use as a papermaking reagent as indicated by the water solubility ("C") and the standard viscosity (5.7 cps).

EXAMPLE 6

Procedures similar to Example 5 were repeated except for the use of LOT-2 as acrylonitrile in lieu of LOT-1. The results are presented in Table 2. The resultant polyacrylamide had quality substantially improved over that obtained in Comparative Example 2, as indicated by its water solubility ("A") and its standard viscosity (5.8 cps).

EXAMPLE 7

Procedures similar to Example 1 were conducted except that the order of the purification columns was changed to arrange "Levatit S-100" as a first column and "Diaion WA-20" as a second column and no activated carbon was used. The results are presented in Table 2. Although the polyacrylamide obtained from the unpurified acrylonitrile in Comparative Example 1 did not have any commercial value, the application of the present invention resulted in a polyacrylamide having quality sufficient for use as a flocculant as indicated by the water solubility ("B") and the standard viscosity (5.7 cps).

EXAMPLE 8

Procedures similar to Example 1 were conducted except that the order of the purification columns was changed to arrange "Calgon CPG" as a first column, "Levatit S-100" as a second column and "Diaion WA-20" as a third column. The results are presented in Table 2. Although the polyacrylamide obtained from the unpurified acrylonitrile in Comparative Example 1 did not have any commercial value, the application of the present invention resulted in a polyacrylamide having quality sufficient for use as a flocculant as indicated by the water solubility ("B") and the standard viscosity (5.s cps).

EXAMPLE 9

Procedures similar to Example 2 were conducted except that the order of the purification columns was changed to arrange "Levatit S-100" as a first column and "Calgon CPG" as a second column and "Diaion WA-20" was not used. The results are presented in Table 2. The resultant polyacrylamide had quality substantially improved over that obtained in Comparative Example 2, as indicated by its water solubility ("A") and its standard viscosity (5.8 cps).

EXAMPLE 10

Procedures similar to Example 7 were conducted except for the use of "Levatit SP-112" as a first column. The results are presented in Table 2. Although the polyacrylamide obtained from the unpurified acrylonitrile in Comparative Example 1 did not have any commercial value, the application of the present invention resulted in a polyacrylamide having quality sufficient for use as a flocculant as indicated by the water solubility ("B") and the standard viscosity (5.7 cps).

EXAMPLE 11

Procedures similar to Example 1 were conducted except for the use of "Levatit SP-112" as a first column. The results are presented in Table 2. Although the polyacrylamide obtained from the unpurified acrylonitrile in Comparative Example 1 did not have any commercial value, the application of the present invention resulted in a polyacrylamide having quality sufficient for use as a flocculant as indicated by the water solubility ("A") and the standard viscosity (5.8 cps).

EXAMPLE 12

The procedures of Example 1 were repeated in a similar manner except for the use of "Levatit OC1059" (gel type) instead of "Diaion WA-20" (porous type) and "Shirasagi LHc" (coconut-shell-base activated carbon) in place of "Calgon CPG" (coal-base activated carbon). The results are presented in Table 2. The results were comparable with those of Example 1 as indicated by its water solubility ("A") and its standard viscosity (5.8 cps).

Comparative Example 3

Procedures similar to Example 1 were conducted except that acrylonitrile (LOT-1) was caused to pass through "Levatit S-100" alone. No improvements were however observed at all as indicated by the water solubility ("D") of the resultant polyacrylamide.

Comparative Example 4

Acrylonitrile having low concentrations of impurities (LOT-1) was percolated through "S-100" alone. The other procedures were conducted as in Example 1. As a result, the water-solubility of the resultant polyacrylamide was ranked as "C". The polyacrylamide conversely had poorer quality compared with that of Comparative Example 2 in which no purification treatment was conducted.

Comparative Examples 5–7

Procedures similar to Example 1 were conducted except that acrylonitrile (LOT-1) was caused to pass through "Diaion WA-20" alone (Comparative Example 5), through "Calgon CPG" alone (Comparative Example 6) or through "Diaion WA-20" and then "Calgon CPG" (Comparative Example 7), respectively. No improvements were however observed at all.

Comparative Examples 8–10

Procedures similar to Example 1 were conducted except that acrylonitrile (LOT-1) was caused to pass through "Diaion WA-20" and then "Levatit S-100" (Comparative Example 8), through "Diaion WA-20", "Calgon CPG" and finally "Levatit S-100" (Comparative Example 9) or through "Calgon CPG" "Diaion WA-20" and finally "Levatit S-100" (Comparative Example 10), respectively. No improvements were however observed at all.

TABLE 1

|  |  | Comparative Example 1 | Example 1 | Comparative Example 2 | Example 2 |
|---|---|---|---|---|---|
| Raw material acrylonitrile |  | LOT-1 Stock solution | LOT-1 Purified solution | LOT-2 Stock solution | LOT-2 Purified solution |
| Acrylonitrile purification column (packing material) |  |  |  |  |  |
| First column |  | None | S-100 | None | S-100 |
| Second column |  | None | WA-20 | None | WA-20 |
| Third column |  | None | CPG | None | CPG |
| Analytical value of acrylonitrile |  |  |  |  |  |
| Acetone | (PPM)[*1] | 11 | 11 | 1.5 | 1.5 |
| Acrolein | (PPM)[*1] | 1.9 | 0.1 | 0.1 | Not detected |
| Acetonitrile | (PPM)[*1] | 77 | 77 | 2 | 2 |
| Oxazole | (PPM)[*1] | 25 | Not detected[*4] | 3 | Not detected |
| Ciscrotonitrile | (PPM)[*1] | 66 | 66 | 5 | 5 |
| Whole aldehydes | (PPM)[*2] | 2.4 | 0.5 | 0.7 | 0.5 |

TABLE 1-continued

|  |  | Comparative Example 1 | Example 1 | Comparative Example 2 | Example 2 |
|---|---|---|---|---|---|
| Peroxide | (PPM)*3 | 0.05 | Not detected | 0.02 | Not detected |
| Physical properties of acrylamide polymer |  |  |  |  |  |
| Water solubility |  | D | A | B | A |
| Salted solution viscosity | (CPS) | Unmeasurable | 5.7 | 5.6 | 5.9 |

TABLE 2

|  | Raw material AN | Purification of acrylonitrile | | | Concentrations of impurities in acrylonitrile (ppm) | | | | Physical properties of polymer | |
|---|---|---|---|---|---|---|---|---|---|---|
|  |  | First column | Second column | Third column | Oxazole | Acrolein | Whole aldehydes | Peroxide | Water solubility | Standard viscosity |
| Example |  |  |  |  |  |  |  |  |  |  |
| 3 | LOT-1 | WA-20 | S-100 | CPG | N.D.* | 0.2 | 0.7 | N.D. | C | 5.7 CPS |
| 4 | LOT-2 | WA-20 | S-100 | CPG | N.D. | N.D. | 0.6 | N.D. | A | 5.8 |
| 5 | LOT-1 | S-100 | CPG | WA-20 | N.D. | 0.1 | 0.6 | N.D. | C | 5.7 |
| 6 | LOT-2 | S-100 | CPG | WA-20 | N.D. | N.D. | 0.5 | N.D. | A | 5.8 |
| 7 | LOT-1 | S-100 | WA-20 | None | N.D. | 0.2 | 0.5 | 0.06 | B | 5.7 |
| 8 | LOT-1 | CPG | S-100 | WA-20 | N.D. | 0.1 | 0.5 | 0.02 | B | 5.8 |
| 9 | LOT-2 | S-100 | CPG | None | N.D. | 0.1 | 0.7 | N.D. | A | 5.8 |
| 10 | LOT-1 | SP-112 | WA-20 | None | N.D. | 0.2 | 0.5 | 0.06 | B | 5.7 |
| 11 | LOT-1 | SP-112 | WA-20 | CPG | N.D. | 0.1 | 0.5 | N.D. | A | 5.8 |
| 12 | LOT-1 | S-100 | OC1059 | Shirasagi LHc | N.D. | 0.1 | 0.6 | N.D. | A | 5.8 |
| Comparative Example |  |  |  |  |  |  |  |  |  |  |
| 3 | LOT-1 | S-100 | None | None | N.D. | 1.9 | 3.4 | 0.07 | D | Unmeasurable |
| 4 | LOT-2 | S-100 | None | None | N.D. | 0.1 | 1.8 | 0.05 | C | 5.6 |
| 5 | LOT-1 | WA-20 | None | None | 25 | 0.2 | 1.9 | 0.05 | D | Unmeasurable |
| 6 | LOT-1 | CPG | None | None | 25 | 1.9 | 2.3 | N.D. | D | Unmeasurable |
| 7 | LOT-1 | WA-20 | CPG | None | 25 | 0.2 | 1.4 | N.D. | D | Unmeasurable |
| 8 | LOT-1 | WA-20 | S-100 | None | N.D. | 0.2 | 3.3 | 0.07 | D | Unmeasurable |
| 9 | LOT-1 | WA-20 | CPG | S-100 | N.D. | 0.2 | 3.3 | 0.04 | D | Unmeasurable |
| 10 | LOT-1 | CPG | WA-20 | S-100 | N.D. | 0.2 | 3.3 | 0.04 | D | Unmeasurable |

*: Not detected.

In Table 1, the asterisked numbers have the following significance:

*1: The concentration was determined by gas chromatography.

*2: The concentration was determined by causing the aldehydes to react with dinitrophenylhydrazin to develop a color and measuring its absorbance.

*3: The concentration was determined by causing the peroxide to react with potassium iodide and measuring its absorbance.

*4: Detectable lower limits of the respective analyses were 1.0 for oxazole, 1.0 for acrolein and 2.0 for acetonitrile, all by ppm.

Acrylonitrile is useful as a raw material for the preparation of acrylamide by catalytic hydration. Acrylonitrile cannot however provide acrylamide of good quality unless it has high quality and contains impurities at low levels. According to the process of the present invention, high-quality acrylamide can be obtained even from acrylonitrile of ordinary quality by conducting only simple column adsorption treatment prior to the catalytic hydration. This acrylamide is particularly useful as a raw material for a flocculant. Further, application of the present invention to acrylonitrile which has been highly distilled and purified and is generally employed for catalytic hydration can provide acrylamide of still higher quality.

We claim:

1. A process for the preparation of acrylamide, which comprises (a) bringing acrylonitrile into contact with a strongly-acidic cation exchange resin and then with at least one of (i) a resin having primary and/or secondary amino groups and (ii) activated carbon, and thereafter (b) subjecting the resultant acrylonitrile to hydration in the presence of a copper-base catalyst.

2. A process according to claim 1, in which (a) comprises bringing acrylonitrile into contact with a strongly-acidic cation exchange resin and then with a resin having primary and/or secondary amino groups.

3. A process according to claim 1, in which (a) comprises bringing acrylonitrile into contact with a strongly-acidic cation exchange resin and then with activated carbon.

4. A process according to claim 1, wherein the acrylonitrile has been prepared by ammoxydation of propylene.

5. A process according to claim 2, wherein after the acrylonitrile has been brought into contact with the resin having primary and/or secondary amino groups, the acrylonitrile is brought into contact with activated carbon.

6. A process according to claim 3, wherein before the acrylonitrile is brought into contact with the strongly-acidic cation exchange resin, the acrylonitrile is brought into contact with the resin having primary and/or secondary amino groups.

7. A process according to claim 3, wherein after the acrylonitrile has been brought into contact with the activated carbon, the acrylonitrile is brought into contact with a resin having primary and/or secondary amino groups.

* * * * *